United States Patent
Abbasi

(10) Patent No.: US 10,423,734 B2
(45) Date of Patent: Sep. 24, 2019

(54) METHOD FOR DETERMINING FILLER TYPES FOR PRESS BENDING OF PIPES

(71) Applicant: Hamid Reza Abbasi, Isfahan (IR)

(72) Inventor: Hamid Reza Abbasi, Isfahan (IR)

( * ) Notice: Subject to any disclaimer, the term of this patent is extended or adjusted under 35 U.S.C. 154(b) by 687 days.

(21) Appl. No.: 15/145,716

(22) Filed: May 3, 2016

(65) Prior Publication Data
US 2017/0320118 A1   Nov. 9, 2017

(51) Int. Cl.
| | | |
|---|---|---|
| B21D 9/01 | (2006.01) |
| G06F 17/50 | (2006.01) |
| G01N 3/02 | (2006.01) |
| B21D 9/12 | (2006.01) |
| G01M 1/00 | (2006.01) |
| G01N 3/08 | (2006.01) |
| G01N 3/12 | (2006.01) |
| G01N 3/20 | (2006.01) |

(52) U.S. Cl.
CPC .......... *G06F 17/5009* (2013.01); *B21D 9/01* (2013.01); *B21D 9/125* (2013.01); *G01M 1/00* (2013.01); *G01N 3/02* (2013.01); *G01N 3/08* (2013.01); *G01N 3/12* (2013.01); *G01N 3/20* (2013.01); *G01N 2203/0075* (2013.01); *G01N 2203/0298* (2013.01)

(58) Field of Classification Search
CPC . B21D 9/01; B21D 9/12; B21D 9/125; B21D 9/15; B21D 9/16
USPC ..................................... 72/466, 466.2, 466.8
See application file for complete search history.

(56) References Cited

U.S. PATENT DOCUMENTS

| | | | | |
|---|---|---|---|---|
| 4,493,203 A | * | 1/1985 | Wheeler .................. | B21D 9/01 72/369 |
| 5,564,303 A | * | 10/1996 | Buchanan ................ | B21D 9/01 72/466 |
| 2006/0053854 A1 | | 3/2006 | Nakazato | |
| 2008/0191470 A1 | | 8/2008 | Esser | |

FOREIGN PATENT DOCUMENTS

| | | |
|---|---|---|
| CN | 201046475 Y | 4/2008 |
| CN | 201744531 U | 2/2011 |
| CN | 102228922 A | 11/2011 |
| CN | 103316974 A | 9/2013 |
| RU | 20080191470 A1 | 11/2008 |

* cited by examiner

*Primary Examiner* — Debra M Sulllivan
(74) *Attorney, Agent, or Firm* — NovoTechIP International PLLC

(57) ABSTRACT

A method for determining elastomer types as pipe filler for pressure bending of a pipe, comprising: selecting a set of elastomer types; obtaining sample pieces from the elastomer types; applying strain test on the sample pieces; determining properties of the sample pieces; calculating strain energy and error function for each sample piece based on an energy model; calculating elastic modulus for each sample piece; selecting elastomer types from the set of elastomer types; analyzing results from the calculation of strain energy, error function and the elastic modulus for the selected elastomer types; simulating the pressure bending process of the pipe, using pipe filler made from the selected elastomer types; and when simulation results indicate an acceptable pressure bent pipe due to the simulated pressure bending, selecting the one or more elastomer types associated with the acceptable pressure bent pipe for the pipe filler.

13 Claims, 14 Drawing Sheets

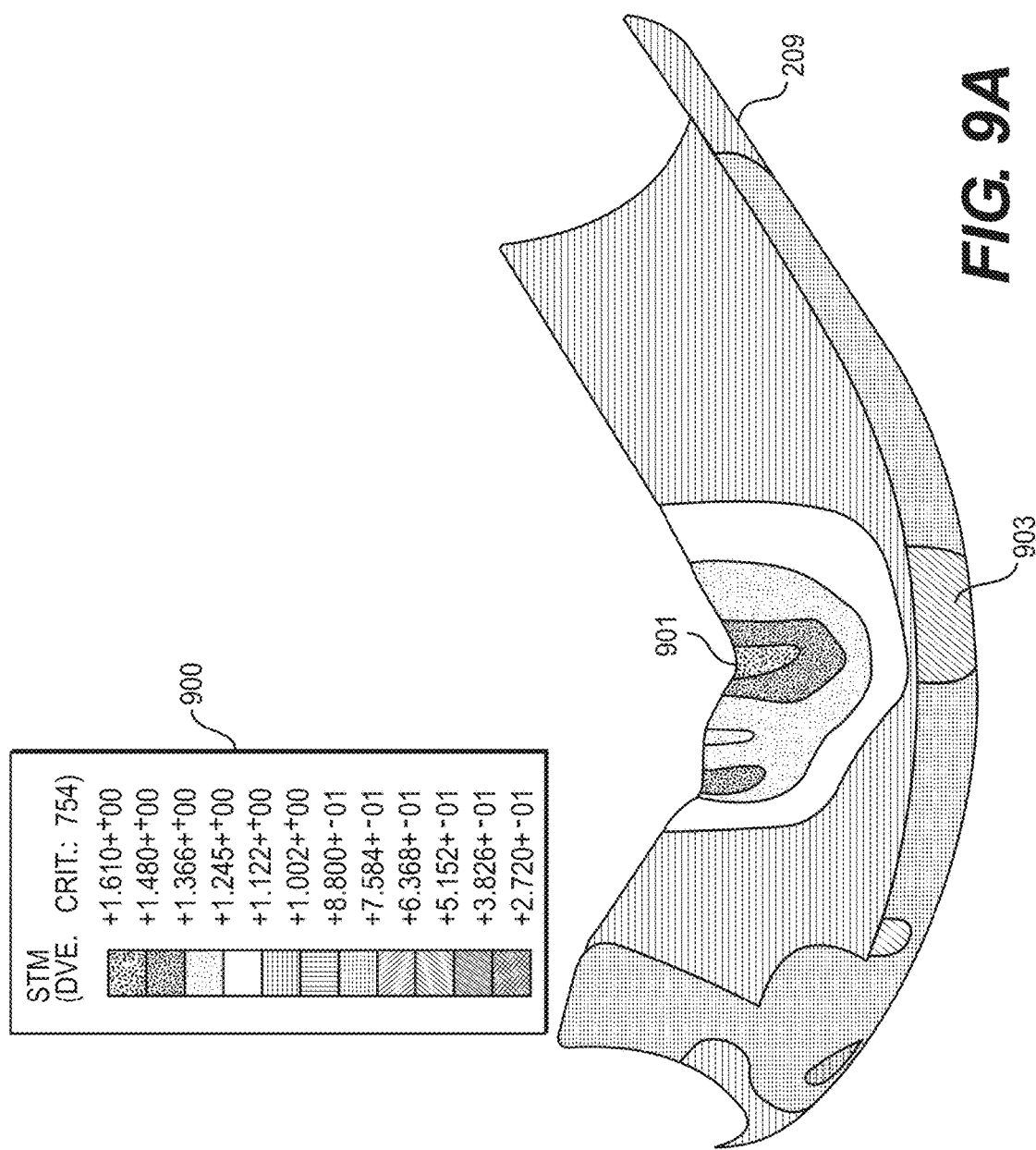

METHOD FOR DETERMINING FILLER TYPES FOR PRESS BENDING OF PIPES

TECHNICAL FIELD

The present application relates generally to pipe bending techniques and, more particularly, to a pipe bending device and method for bending thin-wall pipes with a critical bend radius using press bending methods.

BACKGROUND

Various industries such as land and air transportation vehicle manufacturers, petroleum, power systems, etc., need strong and at the same time light weight components such as, for example, pipes. For example, modern airplanes require high strength-to-weight ratio of components to satisfy the flight performance requirements. Thin-wall pipes with high strength properties made from alloys of aluminum, titanium, stainless steel, etc., are widely used in such industries and are bent with various radiuses and bending angels. In order to reduce weight on the one hand, and volume on the other hand, these pipes are typically formed with minimum bend radius. As a result, due to the specific characteristics of light and thin-walled pipes, conventional bending methods cannot be used for bending such pipes with high bending radiuses (e.g., when bending radius is equivalent of the pipe outside diameter), because bending such pipes using the conventional methods may cause changes in the thickness of the pipe wall, occurrence of tears or wrinkles in the pipe wall, or deformation or upsetting of the pipe.

Therefore, a need exists for device and method for bending thin-wall pipes to prevent damages such as deformation or upsetting, change in the pipe wall thickness and tears or wrinkles to the pipe body. For example, prior to bending a pipe, the pipe can be filled with one or more pieces of flexible material made from elastomers such as, for example, rubber, polyurethane, etc. However, various factors associated with the elastomer fillers can affect the quality of the bent pipe. For example, type, elasticity, and arrangement of pieces of elastomer fillers can affect the bending process and product.

Therefore, a need exists for calculating the filler types, elasticity and arrangement of filler pieces and selecting the filler based on calculation results prior to placing the filler inside the pipe for bending.

SUMMARY

In one general aspect, the instant application describes a method for determining elastomer types to be used as pipe filler for pressure bending of a pipe. The method includes selecting a plurality of elastomer types for making the pipe filler; obtaining sample pieces from the selected plurality of elastomer types; applying strain test on the obtained sample pieces; determining physical properties of the sample pieces based on results of the strain test; selecting an energy model for the sample pieces based on the determined physical properties, wherein the energy model provides relation between the physical properties of each sample piece; calculating strain energy and error function associated with each sample piece, based on the energy model; calculating elastic modulus for each sample piece, based on the energy model, wherein the elastic modulus measures the sample piece resistance to being deformed elastically under a force; selecting one or more elastomer types from the plurality of elastomer types, based on the elastic modulus of the sample pieces; analyzing results from the calculation of strain energy, error function and the elastic modulus for the selected one or more elastomer types; creating a simulation of the pressure bending process of the pipe, using the pipe filler made from a plurality of elastomer pieces from the one or more elastomer types, based on the analyzing results; repeating the selecting the one or more elastomer types, the analyzing, and the creating the simulation, until the simulation results indicate an acceptable pressure bent pipe due to the simulated pressure bending process using the pipe filler made from the plurality of elastomer pieces; and selecting the one or more elastomer types associated with the acceptable pressure bent pipe for the pipe filler.

The above-general aspect may include one or more of the following features. For example, the method may further include proceeding with the pressure bending process of the pipe using the pipe filler made from the selected one or more elastomer types associated with the acceptable pressured bending pipe for the pipe filler, wherein the one or more elastomer types include soft elastomer types, semi-hard elastomer types, hard elastomer types, or a combination thereof. The strain test may include applying strain to the sample pieces with different speeds. The energy model may be a Mooney-Rivlin model, Neo-Hookean model, Yeoh model, or a combination thereof. The simulation may be a software simulation.

The method may further include, prior to proceeding with the pressure bending process, degreasing the exterior of the pipe; anodizing the degreased exterior of the pipe; drying the anodized pipe; applying anti-friction coating material to the dried exterior of the pipe; and heating the pipe. The anti-friction coating may include a solid lubricant, the method may further include, upon heating the pipe, applying a coating of a liquid lubricant to the exterior of the pipe. The pipe may be an aluminum pipe and anodizing may include Sulfuric Acid anodization for providing a conversion on aluminum which changes the surface of the pipe to a naturally occurring aluminum oxide.

The proceeding with the pressure bending process may further include placing the pipe filler inside the pipe; placing the pipe including the pipe filler inside a bending mold; pressing a first end of the pipe toward a bending location within the bending mold by using a ram jack; pressing the pipe filler inside the pipe from a second end of the pipe using a metal mandrel and a mandrel controller ram connected to the metal mandrel; and bending the pipe at the bending location within the bending mold while the pipe filler is pressed within the pipe. The method may further include selecting the bending mold from a molding material different from the pipe material. The molding material may be selected from M2 steel.

The pipe filler may include a plurality of elastomer pieces laid out inside the pipe such that: (i) one or more of the elastomer pieces stuffed at the first end and at the second end of the pipe have a hard type elasticity, (ii) one or more of the elastomer pieces stuffed in middle of the pipe have a soft type elasticity, and (iii) one or more of the elastomer pieces stuffed between the one or more of the elastomer pieces having hard type elasticity and the one or more of the elastomer pieces having soft type elasticity have a semi-hard type elasticity with a hardness between the hard type elasticity and the soft type elasticity.

The diameter of an elastomer piece from the plurality of elastomer pieces is smaller than a diameter of inside of the pipe such that a clearance gap is formed between a pipe wall and the pipe filler. The value of clearance gap may be different for each of the one or more of the elastomer pieces having the hard type elasticity, the one or more of the elastomer pieces having the soft type elasticity, and the one or more of the elastomer pieces having the semi-hard type elasticity.

BRIEF DESCRIPTION OF THE DRAWINGS

Features of the subject technology are set forth in the appended claims. However, for purpose of explanation, several implementations of the subject technology are set forth in the following figures.

FIGS. 9A-9D illustrate simulated results of pressure bending of a pipe, according to various implementations;

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

Figure 1:
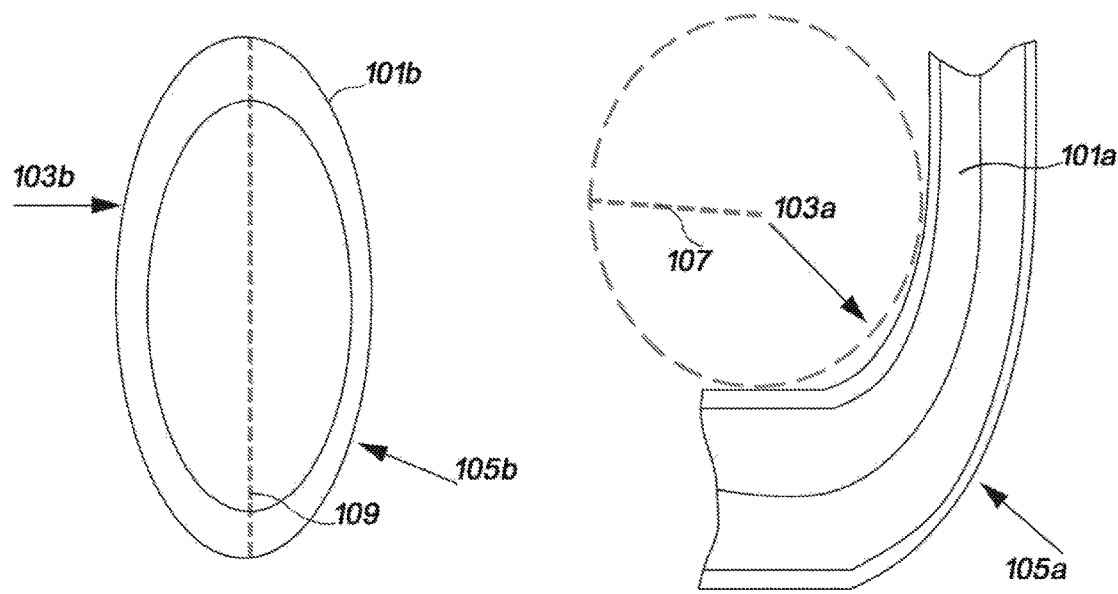
FIG. 1 illustrates problems that can arise during press bending of a thin-wall pipe.

FIG. 1 illustrates problems that can arise during press bending of a thin-wall pipe. Thin-wall pipes with high strength property such as, for example, 304 stainless steel (304), aluminum (Al-6061) and titanium can be bent using a suitable bending method for the pipe material, relative bend radius (R) to the pipe diameter (D) (RID), relative wall thickness (t) to the diameter (t/D) and desired precision.

It is typically preferred that the bend radius of a pipe to be several times greater than the pipe diameter and when a bend radius smaller or equivalent of the pipe diameter is needed, the commonly used cold-bending methods cannot produce a satisfactory result due to damages to the pipe. In such critical bending conditions, pressure bending method can be used to make the pipe with a small bending radius. Pressure bending methods can be used for bending thin-wall pipes with radii down to 1D or equivalent of pipe diameter.

Several types of defects may occur during pressure bending process. For example, wrinkling on the inner side of thin-wall pipe, tearing and/or thinning of the outer side of the bend zone, upsetting and buckling in the straight part of the tube are among the problems that may occur in the pressure bending process. As shown in FIG. 1, when press bending a thin-wall pipe 101$a$, the part 103$a$ of the pipe wall inside the bend is compressed and thickened and may be wrinkled, while the part 105$a$ of the pipe wall outside the bend is stretched and thinned and may beak. 101$b$ is a cross section of pipe 101$a$ in which the internal wall 103$a$ is compressed and the external wall 105$b$ is stretched due to bending.

In cases where the ratio of the bend radius 107 (R) to the outside diameter 109 of the pipe (D) is greater than 3 (R/D>3), the bending of pipe 101$a$ may not cause a problem. However, for critical bends for thin-wall pipes such as aluminum alloy pipes, titanium pipes and stainless steel pipes, where the ratio RID is smaller than 3, the above mentioned damages due to compression and stretching of the pipe may occur. Therefore, methods and devices are needed for bending such pipes without damaging them.

In one implementation, using elastomer fillers can prevent damage to the thin-pipes during critical bending. Elastomer fillers can be used in pressure bending process to control the metal flow by applying internal pressure within the pipe. For a successful bending, fillers with several complexities can be used to obtain suitable operating conditions. For example, instead of using a uniform elastomer filler throughout the pipe, a filler with various elastomer types can be used such that hard elastomer bars used at both ends of the pipe and soft elastomer bars at the middle of the pipe to make a sound and a defect free bend. The process is also highly sensitive to friction conditions of the inner and outer surfaces of the pipe.

Figure 2:
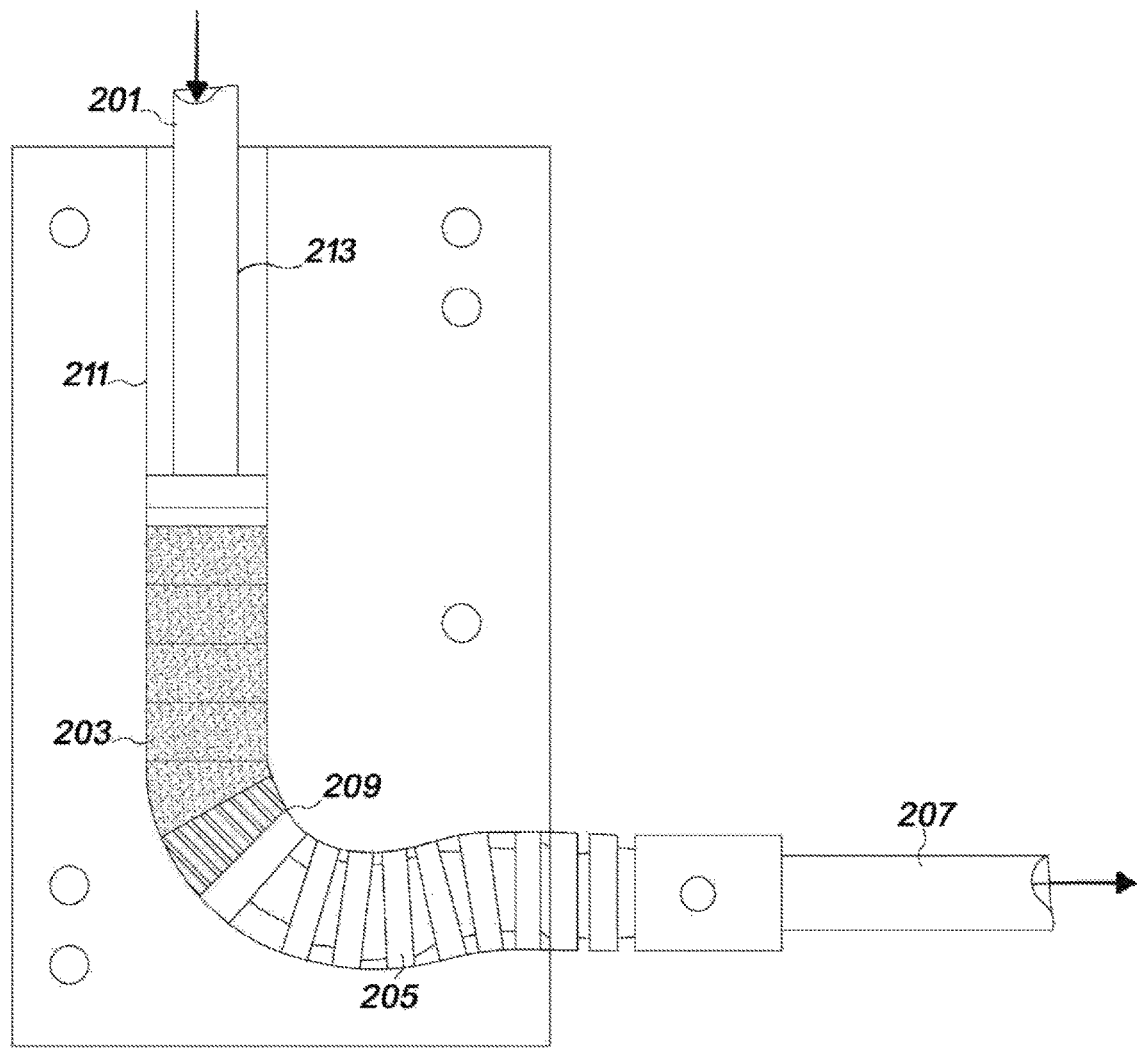
FIG. 2 illustrates a pipe bending device, according to an implementation.

FIG. 2 illustrates a pipe bending device, according to an implementation. Prior to bending a pipe 209, the pipe 209 can be filled with a flexible material 203. The flexible material 203 can be made from elastomers filler such as, for example, rubber, polyurethane, etc. Upon filling the pipe 209 with flexible material 203, the pipe 209 can be placed inside a mold 211. The mold 211 may include a bending configuration designed to receive the pipe 209 and bend the pipe 209 to take the form of the bending configuration within the mold 211.

Once the pipe 209 is fixed inside the mold 211, the pipe 209 may be pressed toward the bending configuration within the mold 211 by a hydraulic ram jack 201 in the direction shown by arrow 213. The hydraulic ram jack 201 may be configured to come into contact with the first end of the pipe 209 and push the first end of the pipe 209 toward the bending configuration within the mold 211. The hydraulic ram jack 201 may have a spherical shape and a diameter slightly larger than the diameter of the pipe 209. The hydraulic ram jack 201 may also include a rubber ball at its end with a diameter about substantially the same size as the pipe 209. The rubber ball may be configured to seal the first end of the pipe 209 to keep the elastomer filler 203 from coming out of the first end as the pipe 209 is pressed toward the bending configuration within the mold 211.

In one implementation, slightly before the bending configuration (e.g., between the bending configuration in the mold 211 and the first end of the pipe), a metal mandrel 205 may be placed and may be held at this position with a holding element. The holding element may include a hydraulic pump. The hydraulic pump may be connected to a mandrel control ram 207 configured to control the movement of the metal mandrel 205. In one example, the mandrel control rain 207 may control the metal mandrel 205 to maintain its position until the applied pressure to the elastomer filler 203 reaches a certain threshold. Once the applied pressure to the elastomer filler 203 reaches the certain threshold, the controller may control the metal mandrel 205 to maintain this pressure while moving toward the molding configuration within the mold 211 as the pipe 209 is pressed toward the molding configuration by the hydraulic ramp jack 201.

In one implementation, the total length of the elastomer filler 203 may be less than the length of the pipe 209. In this implementation, the metal mandrel 205 may have a spherical shape and a diameter smaller than the diameter of the pipe 209. The metal mandrel 205 may be configured to be received within the pipe 209 as the pipe 209 moves toward the bending configuration within the mold 211. In this manner, as the pipe 209 moves toward the bending configuration within the mold 211 by the hydraulic ramp jack 201, the elastomer filler 203 is pressed within the pipe 209 since its movement is stopped by the metal mandrel 205. This may cause the elastomer filler 203 to expand or inflate in the direction of pipe 209 diameter. This expansion can produce pressure towards the walls of the pipe 209. The pressure produced by the expanded elastomer filler 203 perpendicular to the walls of the pipe 209 may prevent undesired deformation of the pipe due to bending. This pressure may also prevent wrinkling and thinning of the pipe 209 wall due to bending. While the elastomer filler 203 is pressed by the hydraulic ram jack 201 on the first end and the metal mandrel 205 on the second end, the pipe 209 can be guided toward the bending configuration by the hydraulic ram jack 201. The pipe 209 is bent in accordance with the bending configuration within the mold 211. The elastomer filler 203 may also take the bent shape of the pipe 209.

In another implementation, the total length of the elastomer filler 203 may be slightly longer than the length of pipe 209 and therefore a piece of elastomer filler 203 may protrude out from the pipe 209. During the bending process, the elastomer filler 203 may behave like a fluid and may be pushed at both ends to be pressed within the pipe 209. In one implementation, the elastomer filler 203 may be pressed such that in the pressed condition each end of the elastomer filler 203 is fully encapsulated within the pipe 209. In another implementation, the elastomer filler 203 may be pressed such that in the pressed condition each end of elastomer filler 203 may still extend out of the pipe 209. In yet another implementation, the elastomer filler 203 may be pressed such that in the pressed condition one end of the elastomer filler 203 is fully encapsulated within the pipe 209 and another end of the elastomer filler 203 extends outside of the pipe 209 in the pressed condition.

The metal mandrel 205 may be connected to a mandrel control ram 207. The mandrel control ram 207 can maintain a constant pressure applied on the elastomer filler 203 during the bending process. In one implementation, once the pressure applied to the elastomer filler 203 reaches a certain threshold, the mandrel control ram 207 instructs the metal mandrel 205 to move back as the pipe 209 is pressed toward the bending configuration within the mold 211 to maintain the constant threshold pressure applied to the elastomer filler 203. In this manner, the pipe 209 along with the compressed elastomer filler 203 enter the bending configuration space within the mold 211 and bend within the mold 211. To this end, the mandrel control ram 207 may be connected to a controller that includes a pressure sensor for sensing the pressure applied to the elastomer filler 203 or the metal mandrel 205.

The elasticity features of the elastomer filler 203 provide flexibility to the elastomer fillers such that when the fillers are taken out of the pipe 209 the elastomers can regain their initial shape and can be reused in further bending processes. The elastomer filler 203 can be made from a combination of multiple layers of various elastomers with different features such as hardness, elasticity, etc. It is noted that the types of elastomer layers used in the elastomer filler 203 and the arrangement of the layers can affect the quality of bend and the effect the bending may have on the pipe shape and the pipe wall thickness. In one implementation, hard and flexible elastomers, for example black Polyvinyl chloride (PVC) can be used on the ends of the elastomer filler 203. The black PVC on one end of the elastomer filler 203 can be in contact with the hydraulic ram jack 201 on one end of the pipe 209 and the black PVC on the other end of the elastomer filler 203 can be in contact with the metal mandrel 205.

The elastomer filler 203 in the middle of the pipe can be selected from a soft elastomer such as, for example, yellow polyurethane. The mid-layer of elastomers position between the hard layers and the soft layer can be selected from elastomers with medium hardness to transfer the pressure force from the hard layer to the soft layer. If the mid-layer elastomer is made from hard elastomer, it may cause deformation of the pipe wall due to pressure and if the mid-layer elastomer is made from soft elastomers, it may not be capable of transferring the pressure force from an end of the pipe 209 to the soft middle layer and this may cause wrinkling in the middle of the pipe 209 at the time of bending. Therefore, the type of the elastomer used as filler 203 in different parts of the pipe 209 may be an important factor in pressure bending. The mid-layer elastomer fillers can be selected from red polyurethane with medium hardness in the midway between a hard elastomer and a soft elastomer.

As previously discussed, pipe 209 may be manufactured from various materials such as, for example, alloys of aluminum, titanium, rust resistant steel, etc. In one implementation, bending of a thin-wall 6061 aluminum alloy pipe 209 is disclosed. The bend factor F (e.g., diameter of the bend) of a pipe 209 with outside diameter $D_{out}$ when the pipe 209 is bent with a bend centerline radius R can be calculated using equation (1):

$$F = R/D_{out} \quad (1)$$

For example, the disclosed method and device can be used for bending the thin-wall 6061 aluminum alloy pipe 209 in critical conditions (e.g., with a critical bend radius where a ratio of central radius to the outside diameter of the pipe is between 1 and 2) wherein the bend factor F is between 1 and 2 ($1 \leq F \leq 2$).

Figure 3:
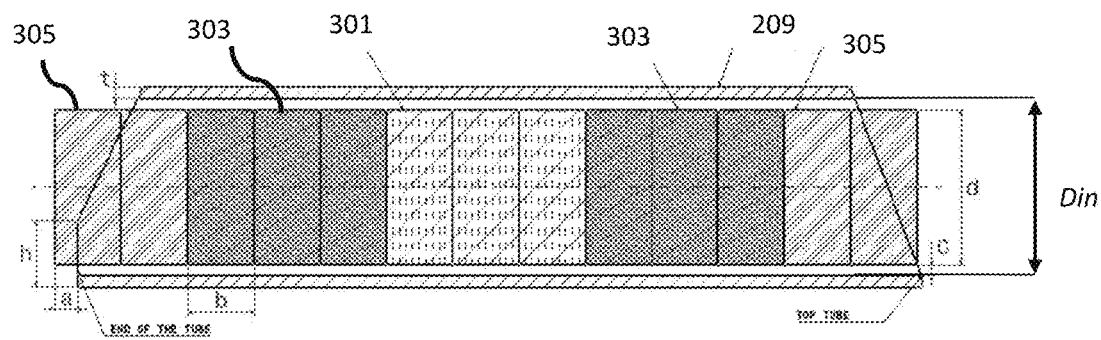
FIG. 3 illustrates arrangement of elastomer filler pieces in a pipe being bent, according to an implementation.

FIG. 3 illustrates arrangement of elastomer filler pieces in a pipe being bent, according to an implementation. In FIG. 3, a pipe 209 includes a wall thickness t and inside diameter $D_{in}$. The elastomer filler pieces 301, 303, and 305 are used to fill the pipe 209 and prepare the pipe for bending. As previously discussed, the elastomer pieces 305 on the ends of pipe 209 are the hard type elastomer, elastomer pieces 301 are soft type elastomer in the middle of the pipe 209 and elastomer pieces 303 are mid-layer elastomers with a medium hardness between hard elastomers 305 and soft elastomers 301. Multiple pieces of each elastomer type can be used, where each piece may have a disk-shape with a thickness shown as b. Each piece of elastomer may have a diameter d, which can be slightly smaller than inside diameter $D_{in}$ of pipe 209, such that a clearance gap c is created between the elastomers and the pipe wall. A total length of the elastomer fillers may be slightly longer than the length of pipe 209 and therefore a piece of elastomer shown as a may protrude out from the pipe 209. During the bending process, the soft elastomer 301 may behave like a fluid and flow towards the ends. However, the hard elastomers 305 prevent the soft elastomer 301 to extrude out of the pipe 209. The elastomers 303 transfer the pressure from hard elastomers 305 to soil elastomers 301.

Vinyl Chloride, used as a medium type elastomer 303, is a resin with high elastic memory. This resin may have a hardness between 55 and 80 on a "Shore D" hardness scale. The modulus of elasticity of the medium type elastomer can be between 15,000 and 25,000 per square inch (psi). Depending on the skill level of an operator performing the pipe bending, this type of medium elastomer can be reused in 200 to 400 cycles of pipe bending process.

The soft elastomer 301 may have high compressibility property. The soft elastomer 301 may be made from natural rubber, synthetic rubber or poly sulphide rubber. The poly sulphide rubber may have a variable hardness between 5 and 85 on a "Shore A" hardness scale. The modulus of elasticity of poly sulphide may be 0.0025 times the modulus elasticity of the medium elastomer. This elastomer may be reused in about 1000 to 2000 cycles of pipe bending process. However, if the medium type elastomer is used throughout the pipe, the elastomer life may be limited to 3 to 10 bending cycles. In addition, it is noted that the modulus elasticity of the medium type elastomer may be a function of the ratio of the diameter to the thickness of the elastomer. The lower the ratio is, the higher the modulus elasticity of the medium type rubber may be. Each piece of elastomer may be resistant to the repeated attrition during the bending cycles. Therefore, sponge type elastomers may not be a suitable elastomer for this purpose because the sponge elastomers tend to tear during the bending process due to uneven attrition forces in different parts of the elastomer. Therefore, porous elastomer types may not be suitable as pipe fillers during pipe bending processes.

The hard elastomer at both ends of the pipe may be under direct pressure from the hydraulic ram jack 201 on one end and the mandrel controller ram 207 on the other end of pipe 209. The hard elastomers may be made from PVC.

The number of pieces of elastomers 301, 303, and 305 can be different depending on the length of pipe 209. The multi piece elastomers may have a longer life compared to a one piece elastomer and can be used repeatedly for extended lengths of time.

The clearance gap c between the elastomers and the pipe wall can be determined based on the elastomer types. In fact, the value of clearance gap c can be different for each elastomer type, hard, soft and medium. In the case of hard and medium type elastomers 303 and 305, if the value of clearance gap c is too small, the pressure from hydraulic ram jack 201 and mandrel controller ram 207 may not be transferred to the soft elastomer 301 in the middle. This may cause wrinkling of the pipe wall at the bend location. On the other hand, if the value of clearance gap c is too large, the soft elastomer may not expand or buckle due to the pressure and instead the soft elastomer may tend to extrude and flow out from the pipe. In this case, too, the pipe may be wrinkled because the pressure cannot be transferred to the bend location.

In the case of soft elastomers 301, if the value of clearance gap c is too low, the pressure transfer may be desirable, however, upon completion of the bending process, removing the elastomer from the pipe may be very difficult. However, a too high clearance gap c may cause the pressure force to be spent on expanding the diameter of the soft elastomer and the pressure is not transferred to the pipe wall and this may cause wrinkling of the pipe wall.

Experimental results show that the total length of the elastomer fillers 301, 303, and 305 need to be slightly longer than the length of pipe 209 such that the hard elastomer 305 protrudes out from pipe 209. The protruding portion of hard elastomer 305 from pipe 209 is shown in FIG. 3 as a. The reason for protruding length a is that elastomers typically retract under pressure and may retract inward inside the pipe 209 for up to 20 millimeters on each side. If the protrusion value a is too large, the hard elastomer 305 may buckle and give way under pressure, however, if the protrusion value a is too small, the elastomer feeling may retract to the point that a pressure from the hydraulic ram jack 201 cannot reach the elastomer filler. In addition, retraction of the elastomer fillers inside the pipe can make removal of the fillers from the pipe at the end of bending process difficult. The experimental results show that the optimal value for the protrusion value a can be between 3 and 4 millimeters.

As previously discussed and shown in FIG. 3, the elastomer filler may consist of individual disk-shaped elastomers laid out inside the pipe 209. In cases when a wrinkling occurs on the pipe wall during the bending process, removing the individual pieces of elastomer from the pipe may become problematic. In order to prevent such problems, a small opening can be created in the center of each disk-shaped elastomer. A thin wire with a diameter slightly smaller than the opening can run through the openings of the disk-shaped elastomers and thread the elastomers together. A thin metal disk with a diameter smaller than the diameter of elastomers can be placed next to the last elastomer 305 on one end of the pipe 209 and one end of the wire can be tied to the metal disks. The other end of the wire can be left untied. Upon completion of the bending process, the elastomer fillers can be removed from the pipe by pulling the untied end of the wire. The diameter of the opening on the disk-shaped elastomer can be about 2 millimeters and the diameter of the wire can be slightly less than the diameter of the opening.

The threading of the elastomer fillers, as discussed, prevents the elastomers from being trapped inside the bent pipe 209. In addition, the treaded elastomer fillers can be used repeatedly for other bending processes for pipes similar to pipe 209 without a need for the fillers to be repeated laid out inside the pipe one by one.

When the elastomers fillers are being laid out next to each other, a layer of fireproof oil or grease can be applied on the touching surfaces of the consecutive disk-shaped elastomer fillers. The grease can create adhesion between the elastomer fillers. The outer surface of the elastomer fillers touching the internal wall of pipe 209 can also be greased. If no grease is applied, a high friction may be generated between the elastomers and the pipe wall and the friction may reduce the pressure inside the pipe. The reduced pressure may affect the bending process by causing wrinkles in the pipe wall.

The degree of roughness of the surface of each elastomer filler can affect the bending process. According to the experiments performed, the optimum value of the $R_a$ factor (e.g., the arithmetic average of absolute values of collected roughness data points) may be from 0.5 to 0.6. ($0.5 \leq R_a \leq 0.6$).

Figure 4:
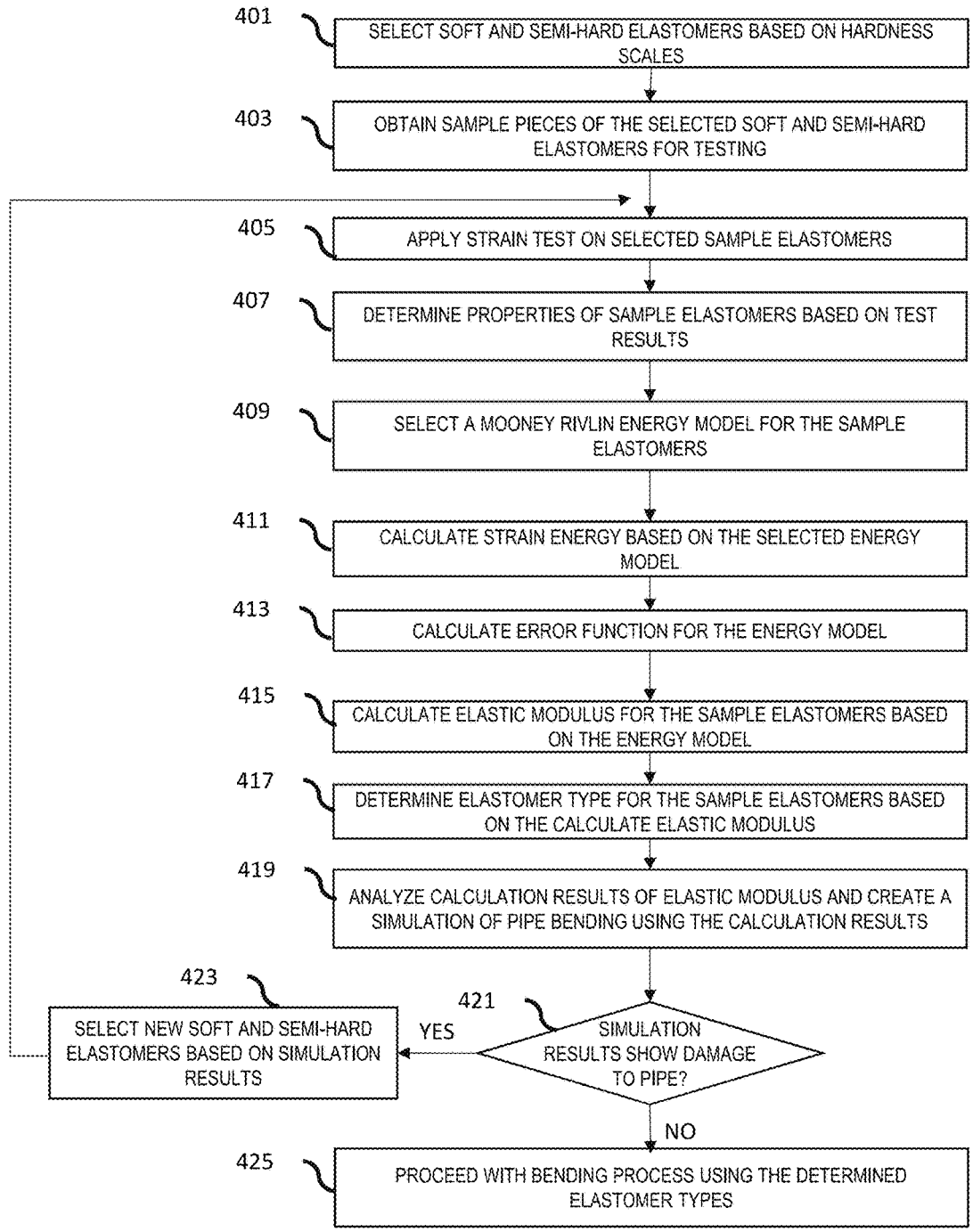
FIG. 4 illustrates a flowchart of a process for determining filler types for press bending of thin-wall pipes, according to an implementation.

FIG. 4 illustrates a flowchart of a process for determining filler types for press bending of thin-wall pipes, according to an implementation. As previously described, the type, characteristics and arrangement of elastomers 301, 303 and 305 (shown in FIG. 3) affect the bend quality of a thin-wall pipe 209. Selecting suitable fillers can prevent damage to the pipe 209 due to compression or stretches during the bending process. The flowchart of FIG. 4 illustrates a method for precise determination of the types of elastomer fillers 301, 303 and 305 prior to stuffing the fillers in pipe 209.

As an example, for an aluminum thin-wall pipe 209, if a one piece soft filler with a hardness 85 in "Shore A" scale is used, the bending process can cause damages to the pipe on both ends. The advantage of the soft elastomer with hardness 85 "Shore A" is that this filler can maintain hydrostatic pressure throughout the pipe, even in the stretched area at the bend location such that at the bend location the pipe body is not separated from the mold 211 (shown in FIG. 2). Therefore, the circular shape of the pipe cross-section at the bend location can be maintained during the bending process.

As another example, for the aluminum thin-wall pipe 209, if a one piece hard filler with a hardness 75 in "Shore D" scale is used, the filler may lose pressure at the bend location and as a result, the pipe 209 may separate from mold 211 and the pipe may be flattened. However, the advantage of the hard elastomer with hardness 75 "Shore D" is that this filler may not cause damage to the pipe ends. Therefore, a soft filler can maintain circular shape of the pipe cross-section at the bend location and a hard filler can prevent damage at both ends of the pipe. A multi piece filler including soft and hard elastomers can be beneficial in reducing or eliminating damages to the pipe during the bending process. However, bends with various degrees may require adjustment of filler types based on calculating various factors such as, for example, friction factor and optimizing the factor.

Referring back to FIG. 4, at block 401, soft, hard and medium (semi-hard) elastomers, for example, with respective hardness 85 "Shore A" and 75 "Shore D", are selected. The hardness of elastomers may be decided based on past experimental results, references, etc. At 403, sample pieces of the selected elastomers are obtained. At block 405, the obtained elastomer sampled are tested by applying strain test on the samples.

Figure 5:
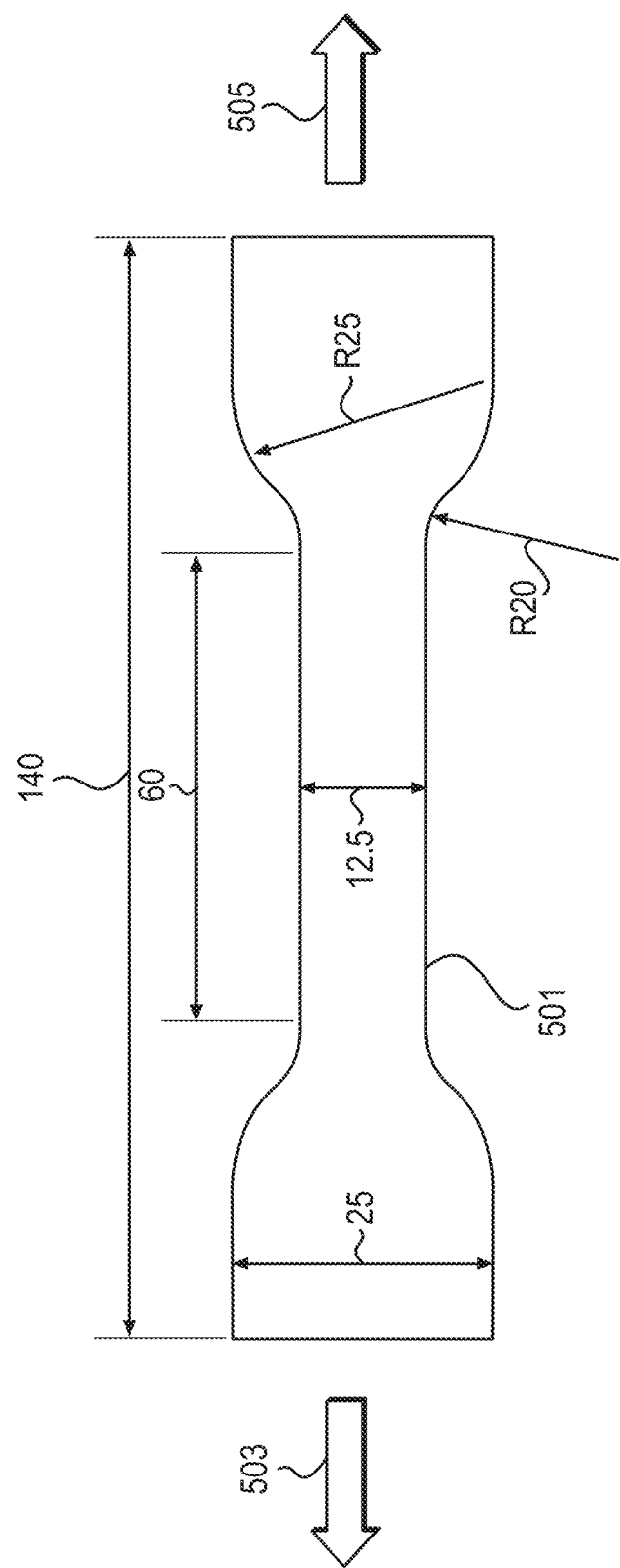
FIG. 5 illustrates a schematic diagram of a strain test.

FIG. 5 illustrates a schematic diagram of a strain test. The strain test can be performed by applying strain on a sample elastomers. For example, a strain or pulling force can be applied to a sample elastomer 501 from opposite directions 503 and 505. The strain test can be repeated with different speeds, for example, a strain with a speed of 240 millimeter per minutes (mm/min), 480 mm/min, etc. For each test, a stress-strain curve can be drawn based on test results. The sample elastomer may have different behavior depending on the strain speed and force. Results from the strain test can be used for determining a stress-strain curve, per block 407.

The stress-strain curve shows a relationship between the stress and strain that the elastomer displays. The curve is unique for each material and is found by recording the amount of deformation (strain) at distinct intervals of tensile or compressive loading (stress). These curves reveal many of the properties of a material, including data to establish the Modulus of elasticity. Modulus of elasticity or elastic modulus of an elastomer is a number that measures the elastomer's resistance to being deformed elastically (i.e., non-permanently) when a force is applied to it. The stress-strain curve determines mechanical characteristics of each elastomer sample.

Stress-strain curves of various materials vary widely, and different tensile tests conducted on the same material may yield different results, depending upon the temperature of the samples and the speed of the loading. It is possible, however, to distinguish some common characteristics among the stress-strain curves of various groups of materials.

Hyper-elastic material models can be classified into three categories, namely, phenomenological or statistical models, mechanistic models, and hybrid of phenomenological and mechanistic models. A phenomenological model is a mathematical expression that relates several different empirical observations of a phenomena to each other, in a way which is consistent with fundamental theory, but may not be directly derived from theory. A phenomenological model foregoes any attempt to explain why the variables interact the way they do, and simply attempts to describe the relationship, with the assumption that the relationship extends past the measured values. Mechanistic models can be driven from arguments about underlying structure of the material.

At block 409, an energy model for the sample elastomers is selected. For example, in one implementation a Mooney-Rivlin energy model (a phenomenological model) can be selected based on experimental results. The Mooney-Rivlin material model is a hyper-elastic material model. The Mooney-Rivlin model is used to determine the elastic response of rubber-like materials. The Mooney-Rivlin model can also be used for calculating the stress-strain relationship of a material with respect to two empirically determined constants C1 and C2, which are also the constants of the deformation tensor.

The Mooney-Rivlin model can be used to determine whether behavior of elastomer material is hyper-elastic or nonlinear. For example, the behavior can be determined for various types of elastomer, soft elastomer (85 shore-A), semi-hard elastomer (75 shore-D), etc.

A strain energy potential (U) factor can be used to relate stress to strain for hyper-elastic material. Unlike elasticity, there is no unique form of factor U for an elastomer with nonlinear behavior. Some common forms for U factor can be the polynomial model, the Ogden model, the Arruda-Boyce model, and the van der Waals model. Simpler forms of the polynomial model are also available, including the Mooney-Rivlin, Neo-Hookean, reduced polynomial, and Yeoh models.

In continuum mechanics, a Mooney-Rivlin solid is a hyper-elastic material model where the strain energy density function is a linear combination of two invariants of the left Cauchy-Green deformation tensor. A Neo-Hookean solid is a hyper-elastic material model, similar to Hooke's law that can be used for predicting the nonlinear stress-strain behavior of materials undergoing large deformations. In contrast to linear elastic materials, the stress-strain curve of a neo-Hookean material is not linear. Instead, the relationship between applied stress and strain is initially linear, but at a certain point the stress-strain curve will plateau. The neo-Hookean model does not account for the dissipative release of energy as heat while straining the material and perfect elasticity is assumed at all stages of deformation. The Yeoh hyper-elastic material model is a phenomenological model for the deformation of nearly incompressible, nonlinear elastic materials such as rubber. The model is based on an observation that the elastic properties of rubber may be described using a strain energy density function which is a power series in the strain invariants $I_1$, $I_2$, $I_3$. The Yeoh model for incompressible rubber is a function only of $I_1$. For compressible rubbers, a dependence on $I_3$ is added on. Since a polynomial form of the strain energy density function is used but all the three invariants of the left Cauchy-Green deformation tensor are not, the Yeoh model is also called the reduced polynomial model.

In some implementations, the polynomial form of the strain energy potential can be used:

$$U = \sum_{i+j=1}^{N} C_{ij}(I_1 - 3)^i (I_2 - 3)^j + \sum_{i=1}^{N} \frac{1}{D_i}(J - 1)^{2i} \quad (2)$$

where, $I_1$, $I_2$ and J are the strain invariants and N, $C_{ij}$, and $D_i$ are material parameters, which may be functions of temperature. The constants ($C_{ij}$) describe the shear behavior of the elastomer material, and the $D_i$ parameters introduce compressibility. When the elastomers are fully incompressible, all the values of $D_i$ would be zero, and the second part of equation (2) can be ignored.

The constants ($C_{ij}$) of the hyper-elastic models can be calibrated by software, using experimental stress-strain data. The constants ($C_{ij}$) are determined through a least-squares-fit procedure, which minimizes the relative error measure in stress. For the nominal-stress-nominal-strain data pairs, the relative error measure is minimized, as shown in equations (3) and (4):

$$E_{rr} = \sum_{i=1}^{n} (1 - T_i^U / T_i^{test})^2 \quad (3)$$

$$\frac{\partial E_{rr}}{\partial c_{ij}} = 0 \quad (4)$$

$T_i^{test}$ is a stress value from the test data, and $T_i^U$ comes from one of the nominal stress expressions derived below in equations (5) and (6):

$$T_i^U = \frac{\partial U}{\partial \lambda_i^U} \quad (5)$$

$$\lambda_i^U = 1 + \varepsilon_i^U \quad (6)$$

where, $\varepsilon_i$ is the nominal strain and $\lambda_i$ is the stretch in the loading direction. The uniaxial tension test is the most common test and is performed by pulling a "dog-bone" specimen with standard dimensions as shown in FIG. 5.

As previously discussed, various models for hyper-elastic material include Mooney-Rivlin model, Neo-Hookean model, Yeoh model, etc. The error functions can be calculated for different models and compared. The constants C1 and C2 (similar to constant ($C_{ij}$) of equation (2) and the stress-strain curves can be prepared for various models and compared. The experimental data suggests that the Mooney-Rivlin model may provide a more accurate model of behavior of the elastomer compared to other models. Upon calculation of the stress and strain values by the strain test, the test results are used in Mooney-Rivlin model to produce the strain energy. Moreover, the error function can be calculated based on equation (7) below:

$$E_{rel} = \sum_{i=1}^{n} \left(1 - \frac{\sigma_T^i}{\sigma_{EX}^i}\right)^2 \quad (7)$$

In equation (7), E is the error function, $\sigma_T$ is the tension value calculated from theoretical tension laws and is a function of constants C1 and C2, $\sigma_{EX}$ is the tension value calculated from experimental tests such as, for example, axial strain and pressure test, planar strain test, pure shear test, volume test, etc. Subsequently, the constants C1 and C2 can be calculated by minimizing the error function according to equation (8):

$$\frac{\partial E}{\partial C_{ij}} = 0 \quad (8)$$

At block 411, the strain energy of the selected sample elastomers is calculated based on the energy model (e.g., Mooney-Rivlin). The calculation may also include calculation of an error function (at block 413), where the error function can be used to determine C1 and C2 constants for the elastomers. In addition, at block 415, the modulus of elasticity of the sample elastomers can be calculated.

At block 417, the calculated modulus of elasticity can be used to determine the elastomer types suitable for bending the thin-wall pipe. For example, in some exemplary implementations, for bending a thin-wall pipe using a soft elastomer with hardness 85 "Shore A", the modulus of elasticity can be calculated at about 18.72 mega-pascal (Mpa), C1 constant value 0.82 and C2 constant value can be 2.30. For a semi-hard elastomer with hardness 75 "Shore D", used as filler for the thin-wall pipe bending, the modulus of elasticity can be about 180 mega-pascal (Mpa), C1 constant value 6 and C2 constant value can be 24.

At block 419, the calculated values for the modulus of elasticity, and constants C1 and C2 can be analyzed and a simulated pipe bending process using the calculated values can be performed. For example, the simulation can be performed on a computing device using a simulation tool that enables performing simulated pipe bending processes using given parameters such as modulus of elasticity, and constants C1 and C2.

Figure 6:
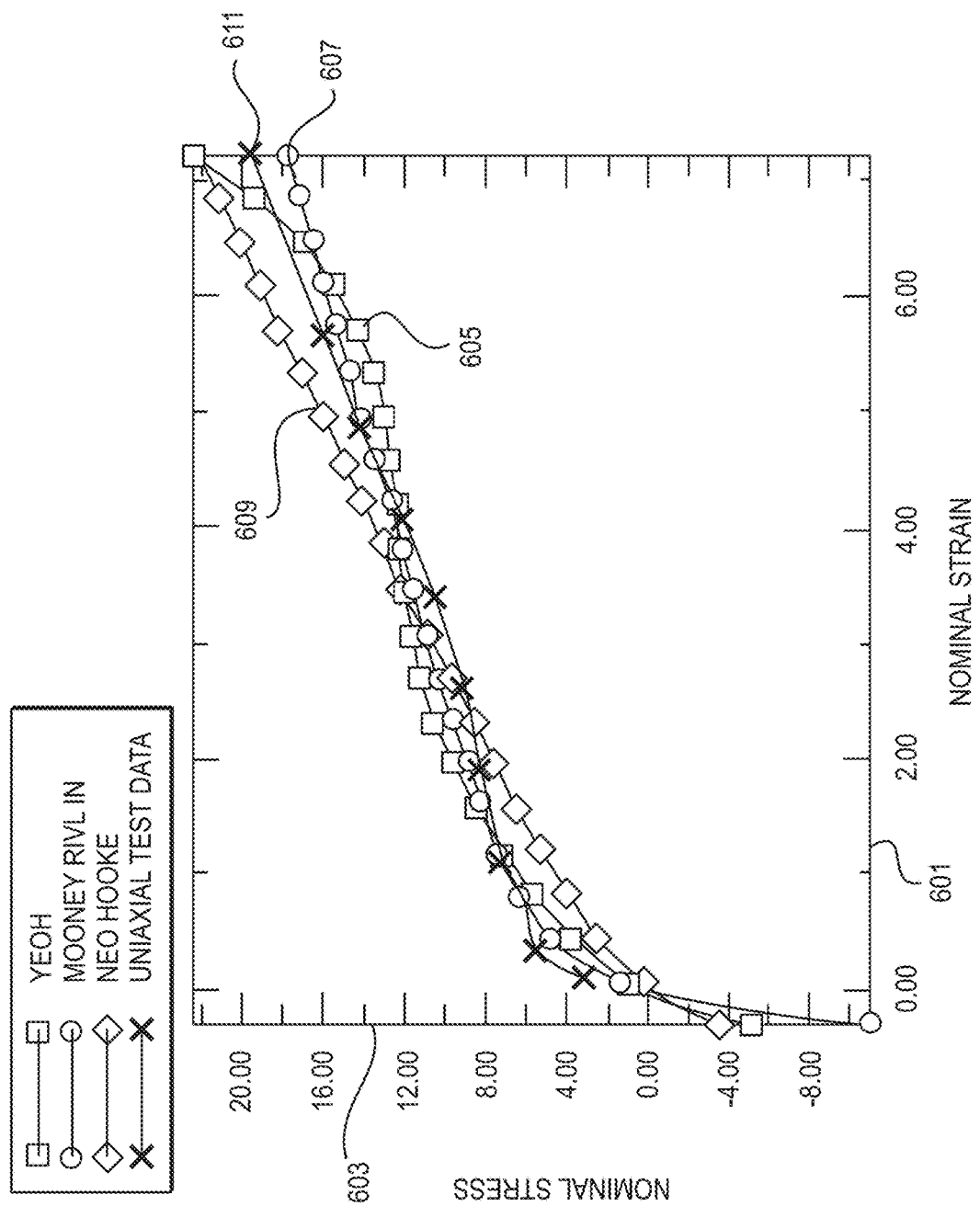
FIG. 6 illustrates a comparison diagram of elastomer behavior models, according to an implementation.

In some implementation, for obtaining a suitable model to represent the elastomer behavior in a pressure bending simulation, various models such as the Yeoh, Mooney-Rivlin and Neo-Hookean models can be used and the results can be compared. FIG. 6 illustrates a comparison diagram of elastomer behavior models, according to an implementation. In FIG. 6, axis 601 represents strain and axis 603 represents the stress of an elastomer calculated based on the Yeoh (curve 605), Mooney-Rivlin (curve 607) and Neo-Hookean (curve 609) models, while curve 611 represent a uniaxial test data. As shown in FIG. 6, the Mooney-Rivlin model (curve 607) gives more desirable results compared to the Yeoh and Neo-Hookean models.

The Mooney-Rivlin model can be defined using the strain energy density function:

$$U = C_{10}(I_1 - 3) + C_{01}(I_2 - 3) + \frac{1}{d}(j - 1)^2 \quad (9)$$

For a soft elastomer, the following constants can be obtained:

$C_{10}$=2.30 MPa $C_{01}$=0.82 MPa (10)

For small to moderate strains ($\varepsilon \ll 1$) tensile modulus can be defined as:

$$E = 6(C_{10} + C_{01}) \quad (11)$$

Hence, for the soft elastomer the elasticity module is equal to 18.7 MPa. For the hard elastomer (75 shore-D) the elasticity module is 180 MPa which is approximately 10 times larger than the soft elastomer. For the hard elastomer making a tensile specimen may not be possible. In such cases, equations (11) and (12) can be used to determine $C_{10}$ and $C_{01}$.

$$C_{01} \approx 0.25 C_{10} \quad (12)$$

Hence, for the hard elastomer, assuming elasticity module is 180 MPa, the following constants can be used.

$$C_{10} = 24 \text{ MPa}$$

$$C_{01} = 6 \text{ MPa} \quad (13)$$

Figure 7:
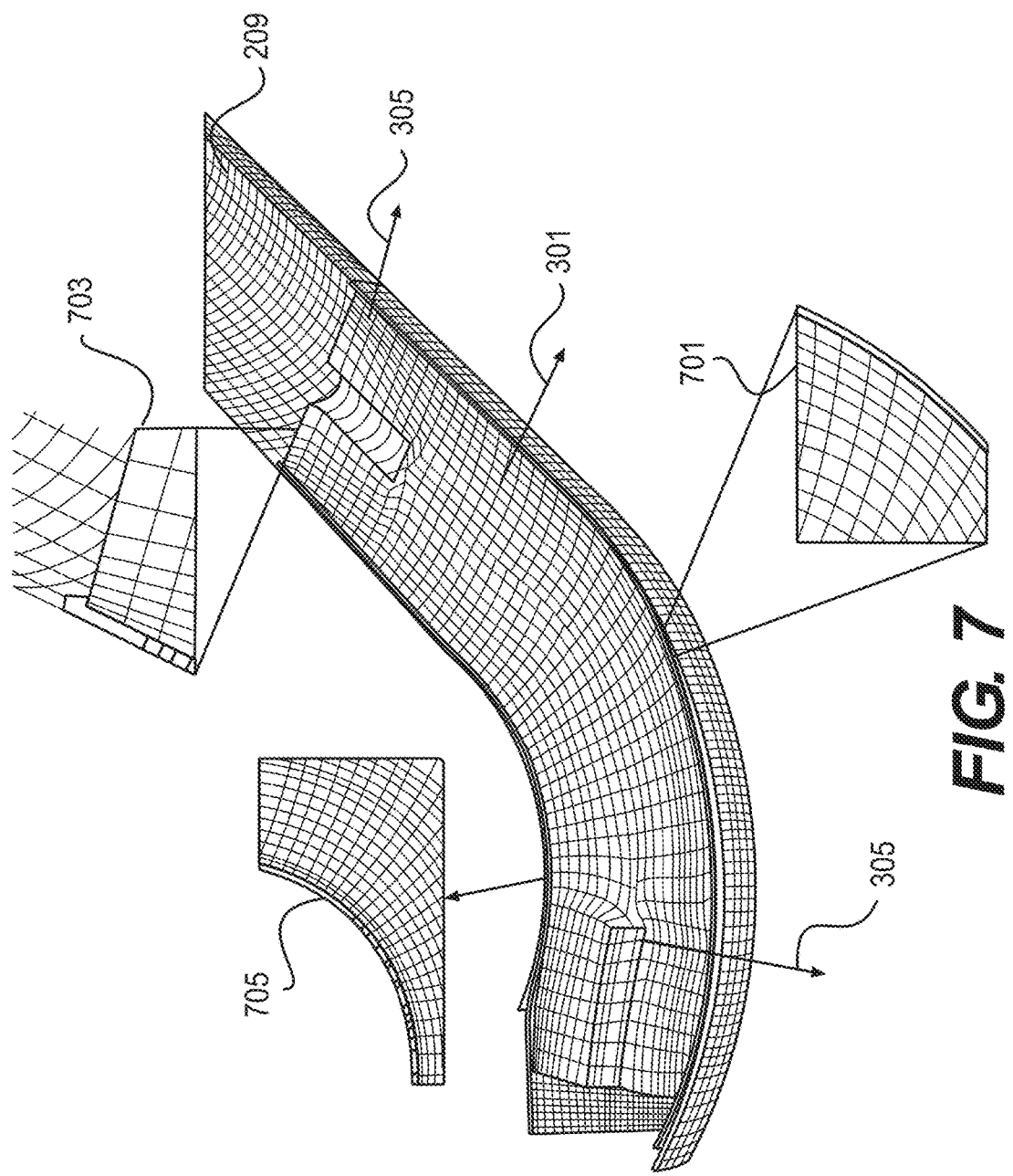
FIG. 7 illustrates using a combination of soft and hard elastomers in the pressure bending process to reduce bending defects, according to an implementation.
Figure 11:
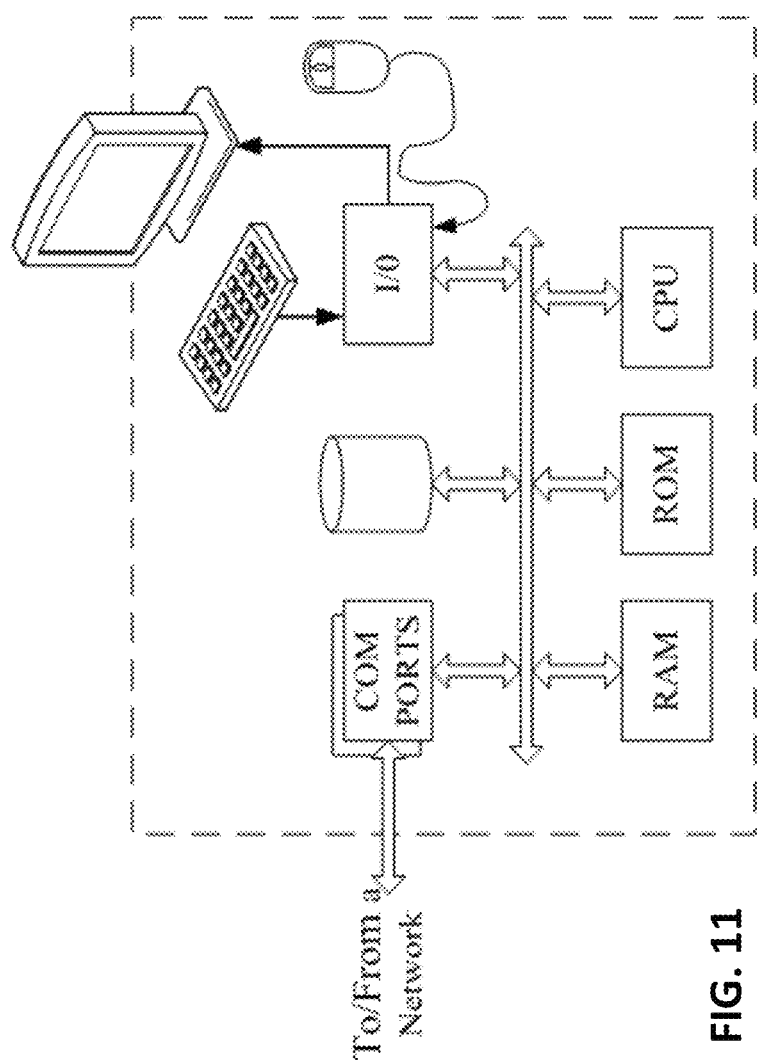
FIG. 11 is a simplified functional block diagram of an exemplary personal computer or customer device that may be used for simulation of pressure bending.

In some implementations, simulation can be performed using Mooney-Rivlin material constants given by equations (11) and (12) on a computing device (shown in FIG. 11). Simulation results show that several types of defects such as upsetting, wrinkling, tearing and flattening can occur using either soft or hard elastomers. One issue that may occur in the pressure bending process is pipe upsetting in the guide zone of the pipe (e.g., a straight part of the pipe in the feed zone). Hence in order to eliminate such defects, combinations of soft and hard elastomers can be used. As previously discussed, hard elastomers (shore D) pieces can be used at the two ends of the pipe and soft elastomer pieces (shore A) can be used in the middle part of the pipe, see FIG. 7. These Simulation results are very well in agreement with experimental observations. FIG. 7 shows that combination of soft and hard rubbers in the push-bending process (hard rubber in the two ends of the tube and soft rubber in the middle of the tube) are helpful in eliminating bending defects.

At block 421, the simulation results are analyzed to determine whether the simulated pipe bending caused any damages to the pipe. If the simulation results determine damage to the pipe during simulation, at block 423 new sample elastomers with different hardness are selected and the process can be repeated from block 405, where the new soft, hard and semi-hard elastomers can be tested. The testing process from step 405 to step 423 can be repeated until the simulation results at step 421 determine no damage or an acceptable damage to the pipe during the simulated bending. In such case, when no damage to pipe occurs, the elastomers 203 can be selected based on the determined elastomer types and at block 425 the pipe bending process can be performed on pipe 209 using elastomers 203 as fillers. The process for determining filler types, as discussed, can prevent trial and error experimentation for determining the filler elastomer types and therefore preventing wasted time and material.

FIG. 7 illustrates using a combination of soft and hard elastomers in the pressure bending process to reduce bending defects. When a combination of soft elastomers 301 and hard elastomers 305 are squeezed during the bending process of a pipe 209, soft elastomer pieces 301 are compressed faster and hence fill the pipe 209 faster than the hard elastomers 305. By using hard elastomer rods 305 at the two ends of pipe 209, higher pressures can be built at the middle of the pipe where hydrostatic stress is required in the bending process. Therefore, bend quality can be improved and bending defects can be reduced when the above mentioned combination of soft and hard elastomers are used.

In addition, simulation results show that using soft elastomer 301 in the middle of the pipe 209 can eliminate flattening defect in the outer region of the pipe 209 where the pipe is under tension (shown as 701) and using hard elastomer 305 at the two ends of the pipe can eliminate upsetting (shown as 703) and wrinkling (shown as 705) of the bent pipe 209.

Figure 8:
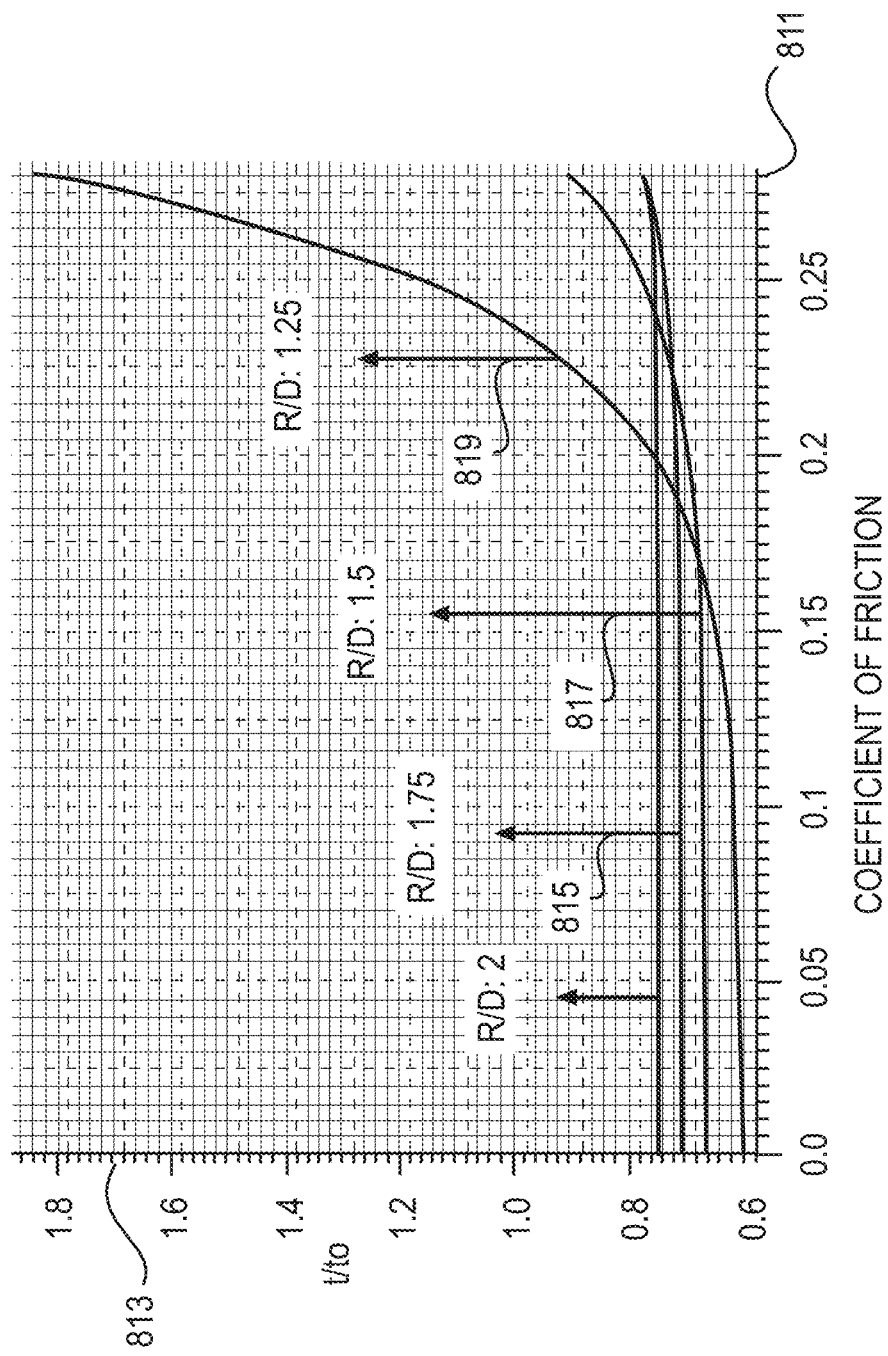
FIG. 8 illustrates relative thickness of outer wall of a pipe versus friction between the pipe and a bending mold, according to an implementation.

In addition to the elastomer types, a friction factor between the thin-wall pipe 209 and the mold 211 may also affect the pipe bending process and the quality of the bent pipe 209. FIG. 8 illustrates relative thickness of outer wall of pipe 209 versus friction between pipe 209 and mold 211. As shown in FIG. 8, as the friction (811) between the pipe 209 and the surface of elbow section of mold 211 increases, relative thickness (813) of outer wall of the bend may also increase. In addition, the rate of increasing the relative thickness 813 is grown by reducing the bend factor (R/D). Therefore, it is possible to bend the pipe with a low bend factor (1<R/D<2) without tearing or thinning in the outer zone of the bend under a suitable friction condition, shown as 815, 817, and 819. 8

The simulation results and the theoretical results in estimating the thickness of the outer wall of the pipe are shown in Table 1. Table 1 illustrates a comparison between the results when R/D=1.5, bend angle=90 degrees and $t_0$=1 mm, ($t_0$ is a primary thickness of the pipe). The comparison of the two results under the different friction conditions shows that the simulation results conform to the theoretical result, so that the simulation result can be used to estimate the thickness distribution in the inner wall of the pipe.

TABLE 1

| coefficient of friction | Numerical estimation of thickness of outer wall of the tube (mm) | Theoretical estimation of thickness of outer wall of the tube (mm) |
| --- | --- | --- |
| 0 | 0.48 | 0.55 |
| 0.1 | 0.58 | 0.63 |
| 0.25 | 0.87 | 0.8 |
| 0.3 | 0.98 | 0.9 |

Figure 9B:
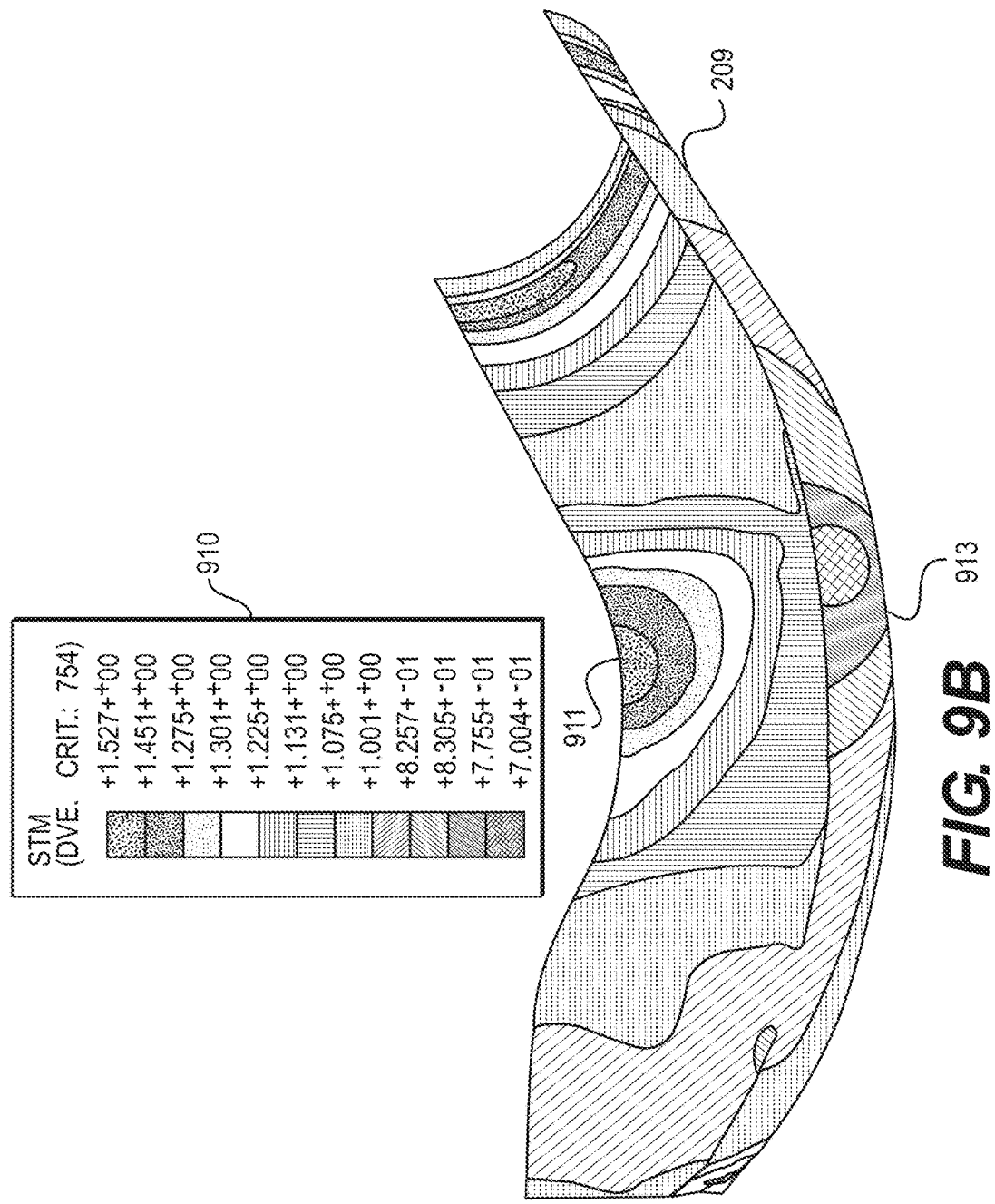
Figure 9C:
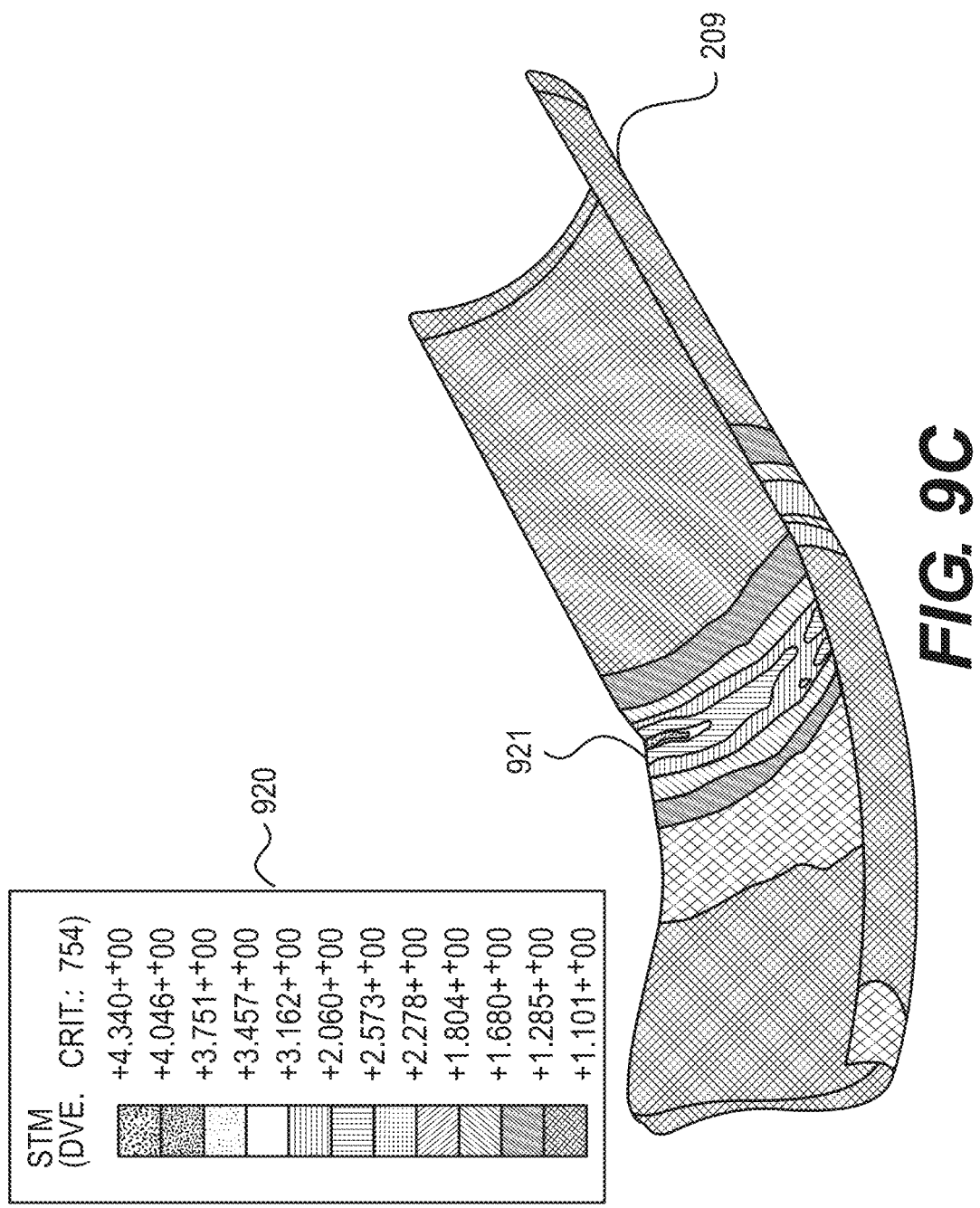

FIGS. 9A-9D illustrate simulated results of pressure bending of a pipe, according to various implementations. A friction between the pipe 209 and a mold 211 can cause buckling or wrinkling in the inner wall of the pipe 209, however, determining the thickness distribution in the bending zone of pipe 209 with an acceptable accuracy using theoretical methods is difficult. Therefore, simulation can be performed, for example, using a computing device. FIGS. 9A-9C illustrate thickness distribution of the pipe 209 under a friction coefficient of 0.1, 0.25 and 0.4 between the pipe 209 and the mold 211. The elastomer fillers are not shown in FIGS. 9A-9C.

Table 900 in FIG. 9A shows the friction values between pipe 209 and a mold 211 (not shown). As shown in FIG. 9A, low friction may cause wrinkling in the inner wall of the pipe 209 at zone 901 and tearing in the outer wall 903 of the pipe. Under a low friction, the thickness of the inner wall can be reduced. Therefore, resistance of the pipe against buckle can be reduced and this can cause a buckle or wrinkling at the inner zone 901. Similarly, if friction between pipe 209 and mold 211 is high (shown in table 920 in FIG. 9C), wrinkling may still appear in the inner zone 921 (shown in FIG. 9C). Since the magnitude of pressure bending force increases by increasing the friction, the force that leads to buckle and wrinkle may appear. Under a suitable friction condition, no wrinkling may happen and no tearing may be seen. As shown in FIG. 9B, no wrinkle appears in the inner wall at zone 911, and no tears at outer wall 913.

Figure 9D:
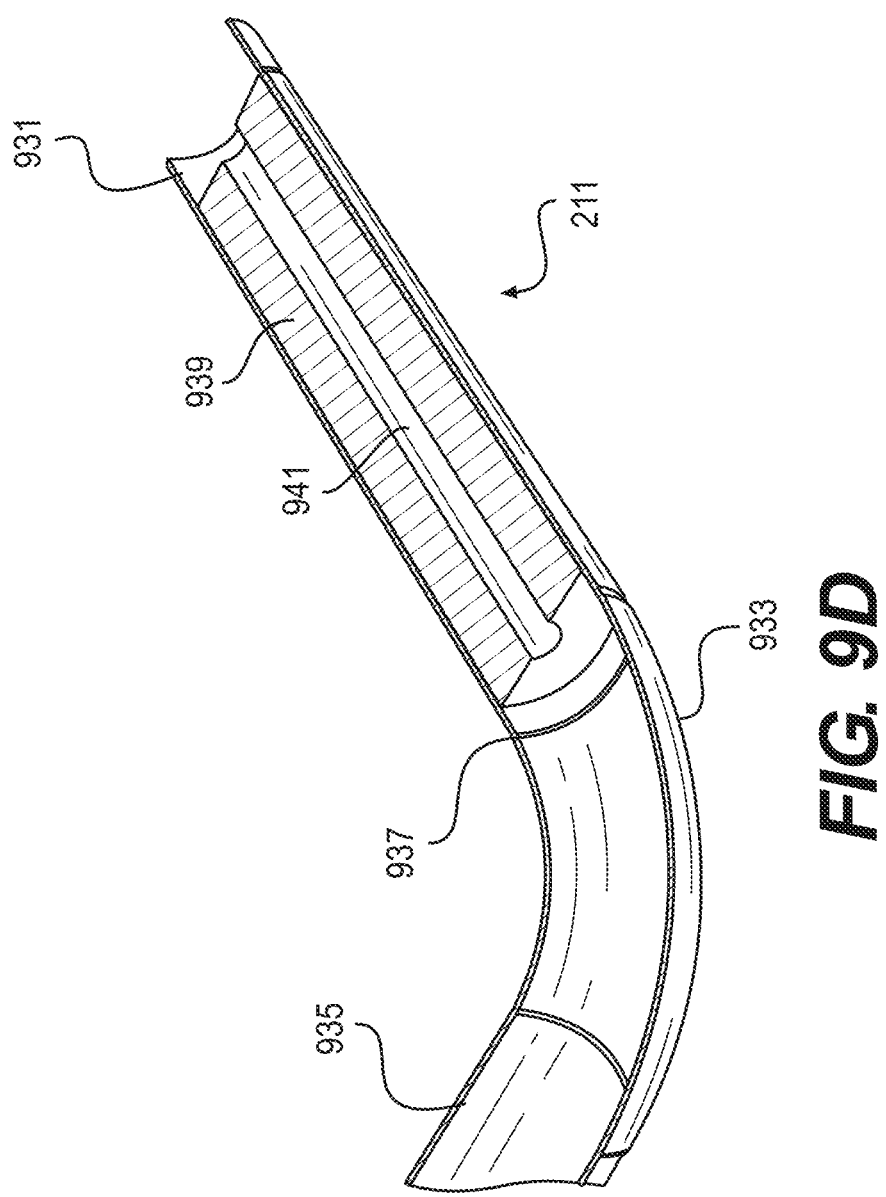

FIG. 9D illustrates a model used in simulation, according to an implementation. As shown in FIG. 9D, the bending mold 211 can be divided into 3 parts, a first straight mold or feeding part 931 to guide a pipe 937 (similar to pipe 209 of FIG. 2) towards an elbow section 933, the elbow section 933, the zone that the pipe 937 takes an elbow shape, and a second straight mold 935 which is used to guide the mandrel 205 (shown in FIG. 2) and bend pipe 209.

The elastomer filler 939 is similar to filler 203 of FIG. 2. In some implementations, a cylinder shape hollow 941 can be considered inside the filler 939. The hollow 941 can create a space for the elastomer elements in the center of the elastomer rod 939 to be squeezed and compressed into the hollow 914, otherwise issues due to incompressible behavior of the elastomer may occur. For example, the compressed elastomer may press into the wall of pipe 209 and create wrinkles in the pipe 209.

The simulation can be performed in two steps. At the first step, an internal pressure applied to the pipe 209 by elastomer 941 can be measured. Maximum internal pressure can be predicted using the following equation (14):

$$P_o = (2 \times S_{ut} \times t_o)/D_o \qquad (14)$$

where $S_{ut}$ is the ultimate tensile strength, $t_o$ and $D_o$ are pipe thickness and pipe diameters, respectively. This equation is the equilibrium of a thin-wall pipe 209 at yielding conditions. Based on the equation 14, for a thin-wall aluminum pipe 209 having a length 180 millimeters (mm), diameter 40 mm, thickness 1 mm, to be bent with a radius 60 mm with a bend angle 90 degrees, value of internal pressure $P_o$ can be estimated to be 12 MPa.

At the second step, pressure bending of pipe 209 can be performed during which the pipe is pressed into the elbow section 933 by the punch (e.g., a hydraulic ram jack 201 of FIG. 2). If the length of feed is 120 mm, the time period for the first step can be 0.2 seconds and 2 seconds for the second step.

Simulation results show that using soft elastomer pieces in the middle of the pipe 209 can keep the pipe in contact with the mold 211 throughout the bending process. Hence, no flattening may occur in the outer region of the pipe, for example, where the pipe is under tension. According to the simulation results, the end part of the pipe which is pushed through the mold can undergo an upsetting process while the other end may suffer from a wrinkling defect.

In some implementations, when a combination of soft and hard elastomers are squeezed inside the pipe 209, the soft elastomer pieces can be compressed earlier than the hard pieces and hence the soft elastomers can fill the tube sooner. By using hard elastomer rods at the two ends of the pipe, higher pressures can be built at the middle of the pipe where hydrostatic stresses are actually needed in the bending process. Therefore bend quality can be improved and bending defects can be better eliminated when the above mentioned combination of soft and hard elastomer pieces are used.

Simulation and experimental results indicate that the friction coefficient between the pipe and the mold must be within a certain range, such that the pipe can be bent without defects. The friction coefficient in the feeding section 931 of the mold (FIG. 9D) must be as low as possible so that collapse may not appear in the head of the pipe 209.

If friction coefficient in the elbow section 933 is very low (less than 0.2), the thickness in the stretch zone may be so thin that wrinkling may appear in the compress zone. Conversely, if friction coefficient in the elbow section 933 is very high (more than 0.3), the wrinkling may still appear in the compress zone. Based on the simulation results and experimental tests, in some implementations, the friction conditions in the bending zone can be optimized to be within the range of 0.2 and 0.3. For example, if the aluminum pipe 209 is covered with a solid lubricant and the surface of the feed section is finished with a machine tool or hand polishing, and the elbow section is finished just in the machining operation, the range of proper friction can be obtained.

Figure 10:
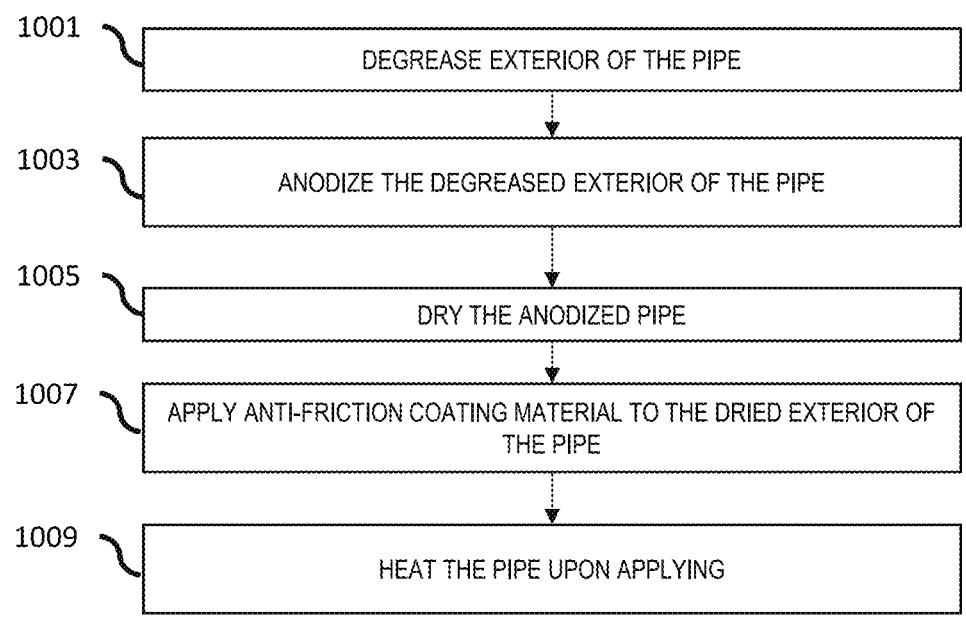
FIG. 10 illustrates a flowchart of a process for lubricating a thin-wall pipe for press bending, according to an implementation.

In order to reduce friction, FIG. 10 illustrates a flowchart of a process for lubricating a thin-wall pipe for press bending, according to an implementation. A solid lubricant can be used for lubricating the exterior of pipe 209 prior to placing the pipe 209 in mold 211. In addition, inside of mold 211 can be made from material different from the material pipe 209 is made from. For example, when pipe 209 is made from aluminum, the inside part of mold 211 can be made from a steel insert (e.g., M2 steel). Application of a solid lubricant on the exterior of pipe 209 and making the mold 211 from steel material can cause the friction factor between pipe 209 and mold 211 to reduce. A reduced friction factor can prevent pipe 209 from being stretched and broke during the bending process. In some instances, for an aluminum pipe 209 (e.g., aluminum 6061) Molybdenum disulfide (Mos2) can be used as the solid lubricant.

Referring back to FIG. 10, at block 1001, pipe 209 is cleaned and degreased. Upon degreasing, at block 1003, the pipe 209 is anodized. The process of anodization prepares the surface of pipe 209 prior to the solid lubricant application. Anodizing is a process that provides a conversion on aluminum, which changes the surface of the material to a naturally occurring aluminum oxide. The oxide build up changes the surface of the aluminum which then provides greater abrasion resistance as well as increased corrosion protection. For example Sulfuric Acid anodization can be performed according to the "MIL-A-8625 Type II Class I" standard. Upon anodization, at block 1005, the pipe 209 is dried in a dryer device (e.g., using a fan).

At block 1007, the pipe 209 is coated with anti-friction material (e.g., Molybdenum disulfide solid lubricant). The solid lubricant prevents corrosion, increases chemical resistance of the aluminum and decreases friction between the pipe 209 and mold 211. Upon application of the anti-friction coating on pipe 209, at block 1009, the pipe is heated. According to the standards, for an aluminum pipe 209 upon application of anti-friction coating, the pipe should be heated to 200±15 degrees centigrade for 30 minutes. The anti-friction coating will cover the pipe 209 with a thickness of 0.005 to 0.013 millimeters. In some cases, upon application of solid lubricant on pipe 209 and prior to placing the pipe 209 in mold 211, a liquid lubricant (e.g., corn oil) can be applied on the pipe 209.

FIG. 11 is a simplified functional block diagram of an exemplary personal computer or customer device that may be used for simulation of pressure bending. FIG. 11 depicts a computing device with user interface elements, as may be used to implement a personal computer or other type of work station or terminal device. The structure, programming and general operation of such computer equipment are well known and as a result the drawings should be self-explanatory.

A computing device, for example, includes a data communication interface for packet data communication. The computing device also includes a central processing unit (CPU), in the form of one or more processors, for executing program instructions. The computing device platform typically includes an internal communication bus, program storage and data storage for various data files to be processed and/or communicated by the computing device, although the computing device often receives programming and data via network communications. The hardware elements, operating systems and programming languages of such computing devices are conventional in nature. Of course, the computing device functions may be implemented in a distributed fashion on a number of similar platforms, to distribute the processing load.

A computer type user terminal device, such as a PC or tablet computer, similarly includes a data communication interface CPU, main memory and one or more mass storage devices for storing user data and the various executable programs (see FIG. 11). A mobile device type user terminal may include similar elements, but will typically use smaller components that also require less power, to facilitate implementation in a portable form factor. The various types of user terminal devices will also include various user input and output elements. A computer, for example, may include a keyboard and a cursor control/selection device such as a mouse, trackball, joystick or touchpad; and a display for visual outputs. A microphone and speaker enable audio input and output. Some smartphones include similar but smaller input and output elements. Tablets and other types of smartphones utilize touch sensitive display screens, instead of separate keyboard and cursor control elements. The hardware elements, operating systems and programming languages of such user terminal devices also are conventional in nature.

Hence, aspects of the methods of providing simulation of pressure bending of a pipe outlined above may be embodied in programming. Program aspects of the technology may be thought of as "products" or "articles of manufacture" typically in the form of executable code and/or associated data that is carried on or embodied in a type of machine readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement simulation of pressure bending of a pipe, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

The separation of various components in the examples described above should not be understood as requiring such separation in all examples, and it should be understood that the described components and systems can generally be integrated together in a single packaged into multiple systems.

While the foregoing has described what are considered to be the best mode and/or other examples, it is understood that various modifications may be made therein and that the subject matter disclosed herein may be implemented in various foil's and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations for the purpose of streamlining the disclosure. This method of disclosure is not to be interpreted as reflecting an intention that the claimed implementations require more features than are expressly recited in each claim. Rather, as the following claims reflect, inventive subject matter lies in less than all features of a single disclosed implementation. Thus the following claims are hereby incorporated into the Detailed Description, with each claim standing on its own as a separately claimed subject matter.

What is claimed is:

1. A method for pressure bending of a pipe, the method comprising:
    selecting a plurality of elastomer types for making the pipe filler;
    obtaining sample pieces from the selected plurality of elastomer types;
    applying strain test on the obtained sample pieces;
    determining physical properties of the sample pieces based on results of the strain test;
    selecting an energy model for the sample pieces based on the determined physical properties, wherein the energy model provides relation between the physical properties of each sample piece;
    calculating strain energy and error function associated with each sample piece, based on the energy model;
    calculating elastic modulus for each sample piece, based on the energy model, wherein the elastic modulus measures the sample piece resistance to being deformed elastically under a force;
    selecting one or more elastomer types from the plurality of elastomer types, based on the elastic modulus of the sample pieces;
    analyzing results from the calculation of strain energy, error function and the elastic modulus for the selected one or more elastomer types;
    creating a simulation of pressure bending process of the pipe, using the pipe filler made from a plurality of elastomer pieces from the one or more elastomer types, based on the analyzing results;
    repeating the selecting the one or more elastomer types, the analyzing, and the creating the simulation, until the simulation results indicate an acceptable pressure bent pipe due to the simulated pressure bending process using the pipe filler made from the plurality of elastomer pieces;
    selecting the one or more elastomer types associated with the acceptable pressure bent pipe for the pipe filler; and
    pressure bending the pipe using the pipe filler made from the selected one or more elastomer types associated with the acceptable pressured bending pipe for the pipe filler, wherein the one or more elastomer types include soft elastomer types, semi-hard elastomer types, hard elastomer types, or a combination thereof.

2. The method of claim 1, wherein the strain test includes applying strain to the sample pieces with different speeds.

3. The method of claim 1, wherein the energy model includes a Mooney-Rivlin model, Neo-Hookean model, Yeoh model, or a combination thereof and is selected based on the determined physical properties of the sample pieces.

4. The method of claim 1, wherein the simulation is a software simulation.

5. The method of claim 1, further comprising:
    prior to pressure bending the pipe:
        degreasing an exterior of the pipe;
        anodizing the degreased exterior of the pipe;
        drying the anodized pipe;
        applying anti-friction coating material to the dried exterior of the pipe; and
        heating the pipe.

6. The method of claim 5, wherein the anti-friction coating includes a solid lubricant, the method further comprising:
    upon heating the pipe, applying a coating of a liquid lubricant to the exterior of the pipe.

7. The method of claim 5, wherein the pipe is an aluminum pipe and anodizing includes Sulfuric Acid anodization for providing a conversion on aluminum which changes a surface of the pipe to a naturally occurring aluminum oxide.

8. The method of claim 1, wherein pressure bending the pipe further includes:
    placing the pipe filler inside the pipe;
    placing the pipe including the pipe filler inside a bending mold;
    pressing a first end of the pipe toward a bending location within the bending mold by using a ram jack;
    pressing the pipe filler inside the pipe from a second end of the pipe using a metal mandrel and a mandrel controller ram connected to the metal mandrel; and
    bending the pipe at the bending location within the bending mold while the pipe filler is pressed within the pipe.

9. The method of claim 8, further comprising:
    selecting the bending mold from a molding material different from the pipe material.

10. The method of claim 9, wherein the molding material is M2 steel.

11. The method of claim 8, wherein:
    the pipe filler made of the plurality of elastomer pieces is laid out inside the pipe such that: (i) one or more of the elastomer pieces stuffed at the first end and at the second end of the pipe have a hard type elasticity, (ii) one or more of the elastomer pieces stuffed in middle of the pipe have a soft type elasticity, and (iii) one or more of the elastomer pieces stuffed between the one or more of the elastomer pieces having hard type elasticity and the one or more of the elastomer pieces having soft type elasticity have a semi-hard type elasticity with a hardness between the hard type elasticity and the soft type elasticity.

12. The method of claim 11, wherein:
    a diameter of each elastomer piece from the plurality of elastomer pieces is smaller than a diameter of inside of the pipe such that a clearance gap is formed between a pipe wall and the pipe filler, and
    a value of clearance gap is different for each of the one or more of the elastomer pieces having the hard type elasticity, the one or more of the elastomer pieces having the soft type elasticity, and the one or more of the elastomer pieces having the semi-hard type elasticity.

13. The method of claim 1, wherein repeating the selecting the one or more elastomer types, the analyzing, and the creating the simulation until the simulation results indicate an acceptable pressure bent pipe includes repeating the selecting the one or more elastomer types, the analyzing, and the creating the simulation until the simulation results indicate no damage to the pipe.

* * * * *